(12) United States Patent
Troxler et al.

(10) Patent No.: US 6,442,232 B2
(45) Date of Patent: *Aug. 27, 2002

(54) THIN LAYER NUCLEAR DENSITY GAUGE

(75) Inventors: Robert E. Troxler, Raleigh; Wewage H. L. Dep, Chapel Hill; John T. Eagan, Cary; Alfred W. Jordan, Raleigh, all of NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/931,545

(22) Filed: Aug. 16, 2001

Related U.S. Application Data

(63) Continuation of application No. 09/518,397, filed on Mar. 2, 2000.
(60) Provisional application No. 60/122,694, filed on Mar. 3, 1999.

(51) Int. Cl.[7] .............................................. G01B 15/02
(52) U.S. Cl. ........................... 378/55; 378/89; 378/207; 250/253
(58) Field of Search ............................... 378/54, 55, 56, 378/86, 89, 90, 203, 207; 250/308, 253

(56) References Cited

U.S. PATENT DOCUMENTS

| | | | |
|---|---|---|---|
| 4,439,675 A | | 3/1984 | Campbell |
| 4,525,854 A | | 7/1985 | Molbert et al. |
| 4,641,030 A | | 2/1987 | Regimand |
| 4,701,868 A | | 10/1987 | Regimand |
| 4,749,858 A | | 6/1988 | Young |
| 4,766,319 A | | 8/1988 | Regimand |
| 4,979,197 A | | 12/1990 | Troxler et al. |
| 6,050,725 A | * | 4/2000 | Regimand .................. 378/207 |
| 6,310,936 B1 | * | 10/2001 | Troxler et al. ............... 378/55 |

FOREIGN PATENT DOCUMENTS

WO     WO 98/57269     12/1998

OTHER PUBLICATIONS

"Troxler Model 3450 RoadReader™ Plus", Troxler Application Brief, Apr. 1997, Troxler Electronic Laboratories, Inc.
"Troxler Model 3450 RoadReader™ Plus"Brochure, Oct. 1997, Troxler Electronic Laboratories, Inc.
Model 3450 RoadReader™ Plus, *Manual of Operation and Instruction*, Dec. 1996, Troxler Electronic Laboratories, Inc.

* cited by examiner

*Primary Examiner*—David P. Porta
*Assistant Examiner*—Therese Barber
(74) *Attorney, Agent, or Firm*—Alston & Bird LLP

(57) ABSTRACT

The present invention provides an improved thin layer nuclear density gauge comprising a gauge housing having a vertical cavity therethrough and a base, a first radiation detector located at a first position within said housing and adjacent to said base of said housing, a second radiation detector located at a second position within said housing and adjacent to said base of said housing, a vertically moveable source rod extending into said cavity of said gauge housing, a radiation source operatively positioned within a distal end of said source rod, at least one bearing operatively positioned to guide said source rod within said cavity, and means for vertically extending and retracting said source rod to a plurality of predetermined source rod positions so as to change the spatial relationship between said radiation source and said first and second radiation detectors. The source rod has a maximum radial movement of less than about 0.003 inch at each predetermined position. The present invention also provides a gauge with an improved radiation shield assembly comprising a sliding block operatively positioned to move laterally between said first position and said second position, a spring engaging said sliding block and biasing said sliding block into said first position, and a fixed block, said fixed block including a track engaging said sliding block and guiding movement of said sliding block.

10 Claims, 5 Drawing Sheets

THIN LAYER NUCLEAR DENSITY GAUGE

CROSS-REFERENCE TO RELATED APPLICATIONS

This application is a continuation of U.S. application Ser. No. 09/518,397, filed Mar. 2, 2000, which claims the benefit of U.S. Provisional Application No. 60/122,694, filed Mar. 3, 1999, both of which are hereby incorporated by reference herein in their entirety.

FIELD OF THE INVENTION

The present invention relates to an apparatus and method for determining the density of materials and, more particularly, relates to an apparatus and method for measuring the density of thin layers of materials.

BACKGROUND OF THE INVENTION

Nuclear radiation gauges have been widely used for measuring the density of soil and asphaltic materials. Such gauges typically include a source of gamma radiation which directs gamma radiation into the test material, and a radiation detector located adjacent to the surface of the test material for detecting radiation scattered back to the surface. From this detector reading, a determination of the density of the material can be made.

These gauges are generally designed to operate either in a "backscatter" mode or in both a backscatter mode and direct transmission mode. In gauges capable of direct transmission mode, the radiation source is vertically moveable from a backscatter position, where it resides within the gauge housing, to a series of direct transmission positions, where it is inserted into small holes or bores in the test specimen.

Many of the gauges commonly in use for measuring density of soil, asphalt and other materials are most effective in measuring densities of materials over depths of approximately 4–6 inches. However, with the increase in cost of paving materials, the practice in maintaining and resurfacing paved roadbeds has become one of applying relatively thin layers or overlays having a thickness of one to three inches. With layers of such a thickness range, many density gauges are ineffective for measuring the density of the overlay because the density reading obtained from such gauges reflects not only the density of the thin layer, but also the density of the underlying base material.

Nuclear gauges capable of measuring the density of thin layers of materials have been developed by the assignee of the present invention. For example, thin layer density gauges are disclosed in U.S. Pat. Nos. 4,525,854, 4,701,868, and 4,641,030, all of which are assigned to the assignee of the present invention and are incorporated herein by reference in their entirety. The gauges disclosed in the above-referenced patents are referred to as "backscatter" gauges because the radiation source does not move outside the gauge housing, which is necessary for measurement in the direct transmission mode.

As disclosed in the above patents, the preferred method of measuring the density of thin layers of materials, such as asphalt, requires two independent density measurement systems. The geometry of these two measurement systems must be configured with respect to one another and with respect to the medium being measured in such a manner that they measure two different volumes of material. The two different volumes are not mutually exclusive insofar as they partially overlap one another. Measurement accuracy depends upon a larger portion of the volume measured by one of the measurement systems being distributed at a lower depth beneath the gauge than the volume measured by the other measurement system. This is accomplished by placing one radiation detection system in closer spatial proximity to the radiation source than the other detection system.

There remains a need in the art for a nuclear gauge capable of operating in both backscatter mode and direct transmission mode, and which is suitable for measuring the density of thin layers of material.

SUMMARY OF THE INVENTION

The present invention provides a nuclear density gauge capable of operating in both backscatter and direct transmission modes and also capable of accurately measuring the density of thin layers of materials. The nuclear gauge of the present invention minimizes the effect of variance in radiation source positioning on the accuracy of the density reading. The source rod of the nuclear gauge of the present invention has a maximum radial movement of less than about 0.003 inch at each predetermined source rod position and, preferably, a maximum radial movement of less than about 0.002 inch. Additionally, the source rod of the nuclear gauge of the present invention has a maximum vertical movement of less than about 0.003 inch at each predetermined source rod position and, preferably, a maximum vertical movement of less than about 0.002 inch.

The nuclear gauge of the present invention is suitable for measuring the density of the thin layer of material overlying a base material and comprises a gauge housing having a vertical cavity therethrough and a base. Within said housing, first and second radiation detectors are located, both detectors being positioned adjacent to the base of the gauge housing. The two radiation detectors are in separate positions within the gauge housing. The gauge further comprises a vertically moveable source rod extending into the cavity of the gauge housing. The source rod contains a radiation source within a distal end thereof. The gauge further comprises at least one bearing operatively positioned to guide the source rod within the vertical cavity of the gauge housing. The gauge also includes means for vertically extending and retracting the source rod to a plurality of predetermined source rod positions so as to change the spatial relationship between the radiation source and the two radiation detectors.

Preferably, the means for vertically extending and retracting the source rod includes an index rod operatively positioned adjacent to the source rod. The index rod has a plurality of notches, each of the notches corresponding to one of the predetermined source rod positions. The means for extending and retracting further comprises a handle affixed to the source rod. The handle includes a cavity therethrough and an indexer. The index rod extends into the cavity of the handle and the indexer is operatively positioned for engaging the notches of the index rod in order to temporarily affix the source rod in one of the predetermined positions. Preferably, at least two pins are used to affix the handle to the source rod. A spring is preferably used to bias the indexer into engagement with the notches of the index rod. For example, a spring having a spring rate of at least about 20 lbs. per inch may be used. In a preferred embodiment, the index rod has a substantially cylindrical shape extending from a distal end of the rod to the position of a notch of the index rod corresponding to the backscatter position.

The gauge also comprises a safety shield coaxially mounted around the vertical cavity of the gauge housing.

The safety shield includes a bearing operatively positioned to guide the source rod through the vertical cavity.

Additionally, the nuclear gauge preferably comprises a radiation shield assembly operatively positioned to move laterally between two positions; a first position blocking a distal end of the vertical cavity of the gauge housing such that radiation is shielded from exiting the cavity and a second position adjacent to the vertical cavity and allowing vertical movement therethrough. In a preferred embodiment, the radiation shield assembly comprising a sliding block operatively positioned to move laterally between the first position and the second position, a spring engaging the sliding block and biasing the sliding block into the first position, and a fixed block. The fixed block preferably includes a track engaging the sliding block and guiding movement of the sliding block. Advantageously, a ball plunger engages the sliding block, and is operatively positioned to prevent vertical movement of the sliding block at the sliding block moves laterally between the first and second positions. A spring engages the ball plunger and biases the ball plunger towards the sliding block. This spring preferably has a spring rate of at least about 50 lbs. per inch.

BRIEF DESCRIPTION OF THE DRAWINGS

Figure 1:
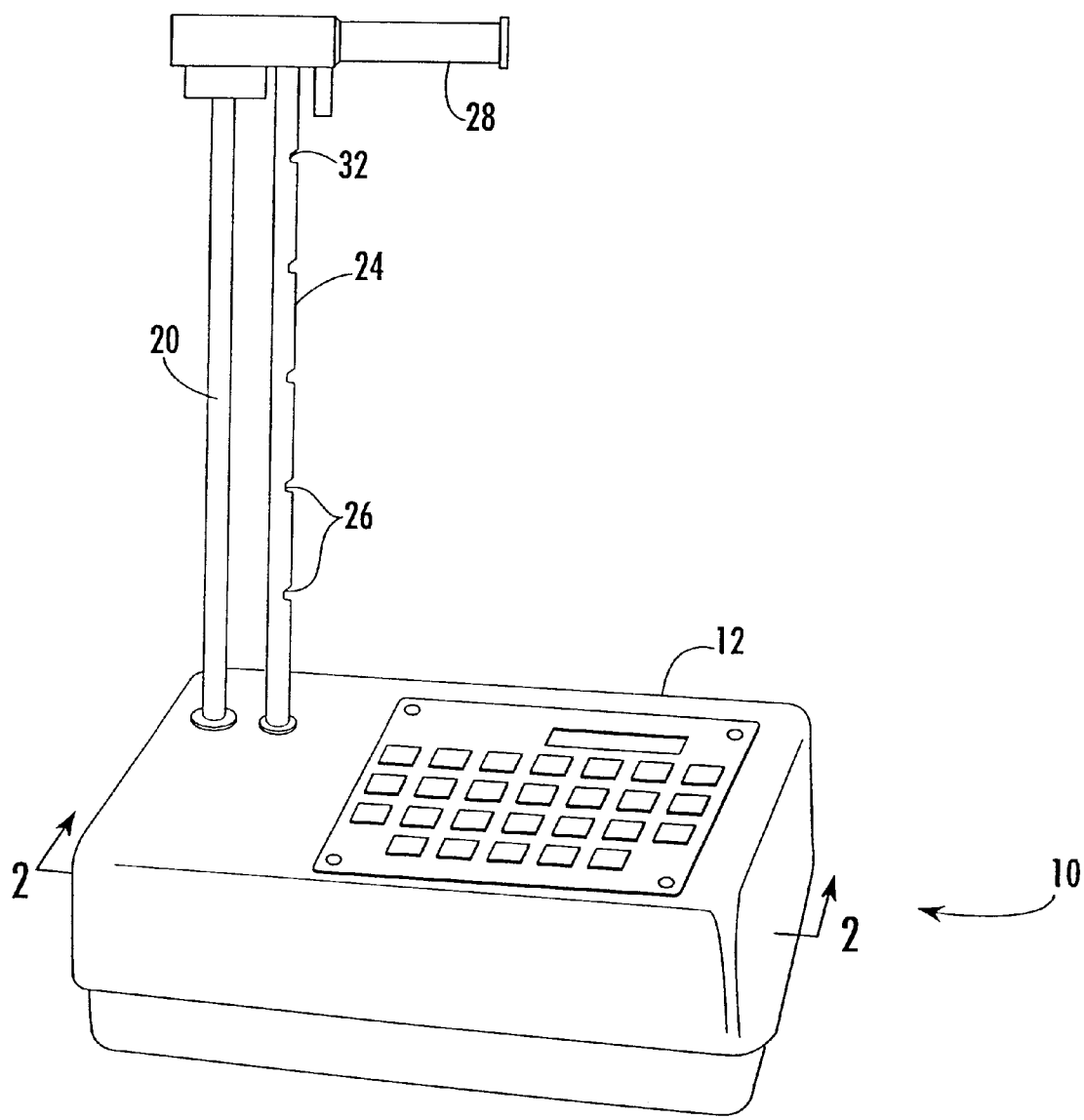
Figure 2:
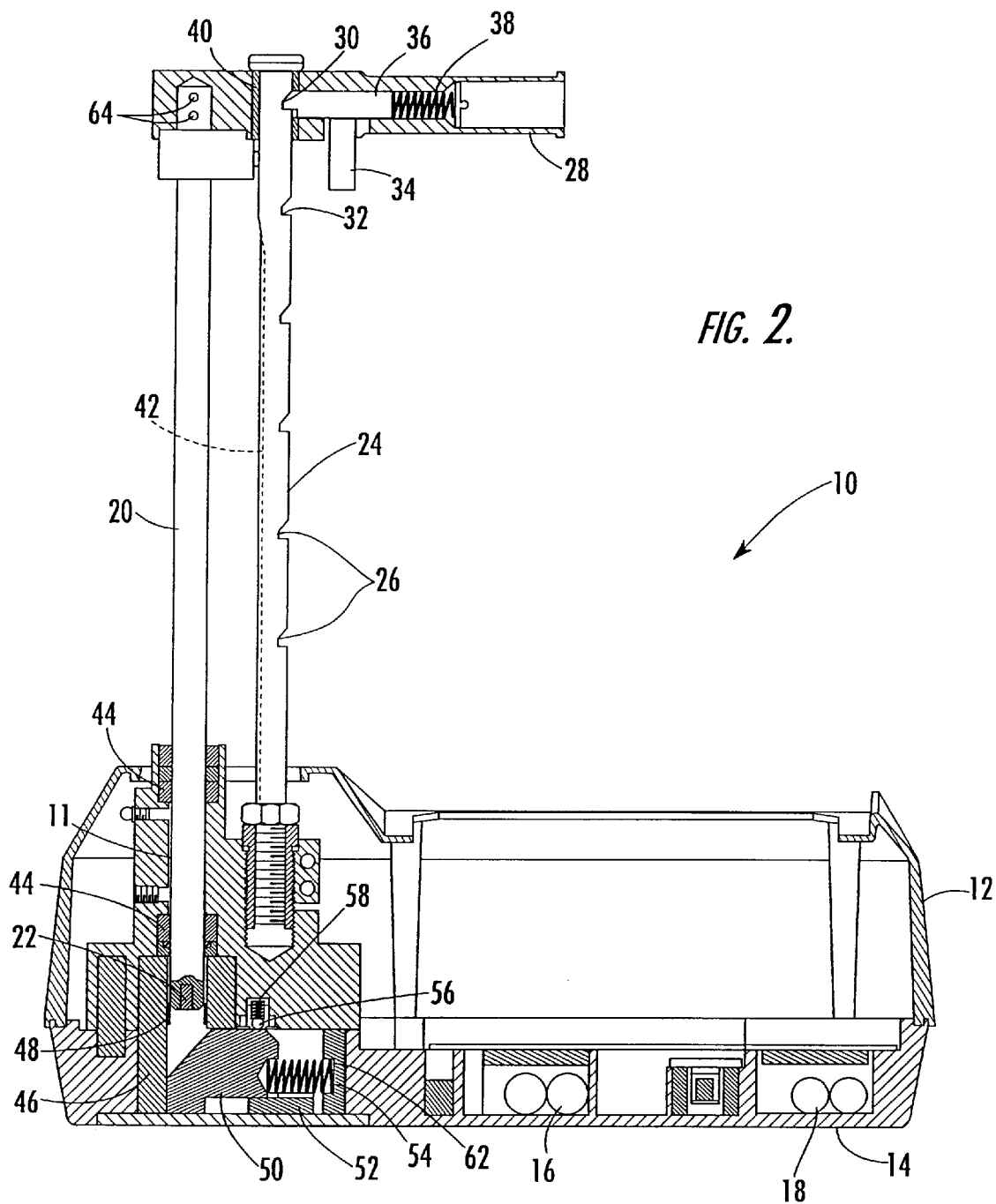
Figure 3A:
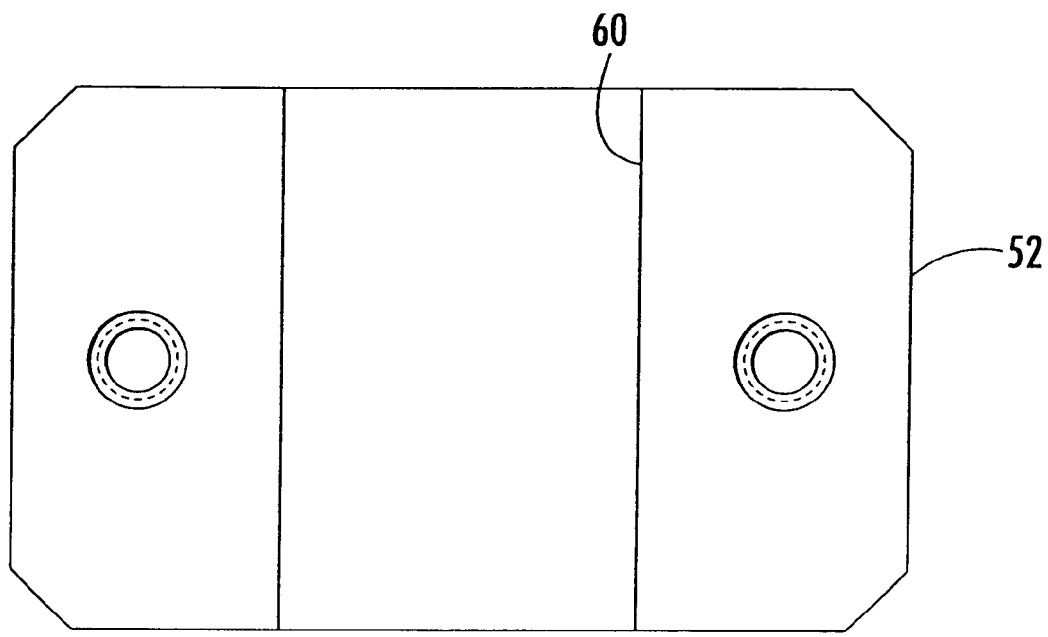
Figure 3B:
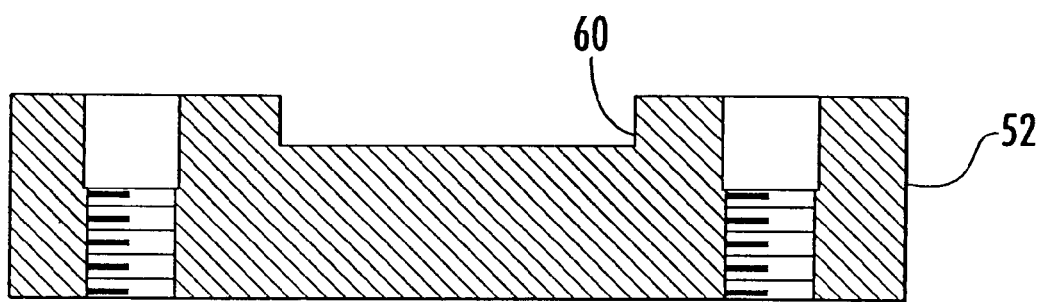
Figure 4A:
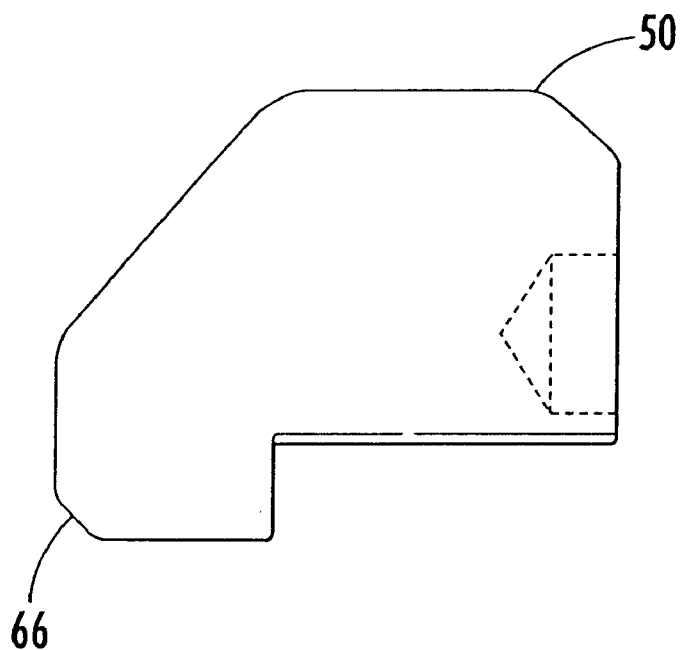
Figure 4B:
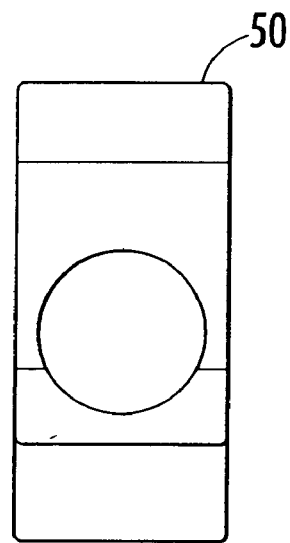
Figure 5A:
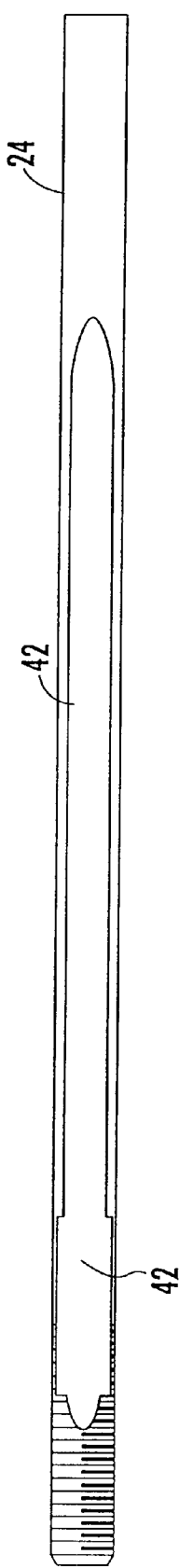
Figure 5B:
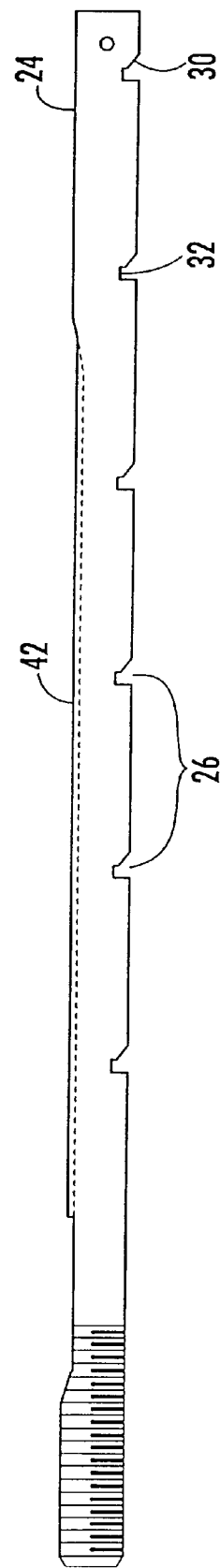

Having thus described the invention in general terms, reference will now be made to the accompanying drawings, which are not necessarily drawn to scale, and wherein:

FIG. 1 is a perspective view of a nuclear gauge according to the present invention;

FIG. 2 is a cross-sectional view of a gauge according to the present invention taken along line 2—2 of FIG. 1;

FIGS. 3A and 3B illustrate the top and side views of the fixed block portion of the gauge of the present invention;

FIGS. 4A and 4B illustrate two side views of the sliding block portion of the gauge of the present invention; and FIGS. 5A and 5B shows two side views of the index rod portion of the gauge of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention provides a nuclear gauge 10 as shown in FIG. 1. The gauge 10 is capable of accurately measuring the density of thin layers of materials, such as asphalt. The gauge 10 can operate in both backscatter and direct transmission modes.

Operation of the gauge is more clearly illustrated by FIG. 2. As shown in FIG. 2, the gauge 10 of the present invention includes a vertically moveable source rod 20 containing a radiation source 22 in a distal end thereof. The radiation source 22 may be any suitable radiation source, such as $^{137}Cs$ radiation source. The source rod 20 extends into a vertical cavity 11 in the gauge housing 12. Bearings 44 are operatively positioned to guide the source rod 20 through the cavity 11 in the gauge housing 12.

As shown, the gauge 10 of the present invention contains two separate density measurement systems. The gauge 10 contains a first pair of radiation detectors 16 and a second pair of radiation detectors 18, wherein the first radiation detectors are located in closer spatial proximity to the radiation source 22. The radiation detectors, 16 and 18, may be any type of gamma ray radiation detector known in the art. Preferably, the radiation detectors, 16 and 18, are Geiger Mueller tubes. The radiation detectors, 16 and 18, are preferably located adjacent to the base 14 of the gauge housing 12.

The gauge 10 also includes means for vertically extending and retracting the source rod 20 to a plurality of predetermined source rod positions so as to change the spatial relationship between the radiation source 22 and the radiation detectors, 16 and 18. The predetermined positions may include, for example, a backscatter position as well as a plurality of direct transmission positions, wherein the radiation source 22 is positioned below the base 14 of the gauge housing 12.

Preferably, the means for extending and retracting comprise an index rod 24 operatively positioned adjacent to the source rod 20. The index rod 24 includes a plurality of notches 26. Each notch 26 corresponds to a predetermined source rod position. For example, one notch 30 corresponds to the "safe" position wherein the radiation source 22 is raised and shielded from the test material. The safe position is used to determine the standard count. Another notch 32 corresponds to the backscatter mode wherein the radiation source 22 is located adjacent to the surface of the test material underlying the gauge 10. Advantageously, the index rod 24 includes flat side 42 where a resistive depth strip (not shown) may be affixed.

The means for vertically extending and retracting the source rod 20 also includes a handle 28 affixed to the source rod. The index rod 24 extends into a cavity 40 in the handle 28. The handle further comprises an indexer 36 operatively positioned for engaging the notches 26 of the index rod 24 in order to temporarily affix the source rod 20 in one of the predetermined positions. The indexer 36 is biased into engagement with the notches 26. Preferably, the indexer 36 is biased into engagement by a spring 38. A trigger 34 allows the user to move the indexer 36 into and out of engagement with the notches 26.

The gauge 10 also includes a safety shield 46 coaxially mounted around the vertical cavity 11 and operatively positioned to minimize the user's exposure to radiation when the radiation source 22 is in the safe position. Preferably, the safety shield 46 is constructed of lead or tungsten. However, other radiation shielding material may be used without departing from the present invention.

It has been discovered that slight inconsistencies in radiation source 22 positioning can result in unacceptable levels of variance in thin layer densities measured by a nuclear gauge. These inconsistencies can manifest themselves both during the actual density measurement counts and also during acquisition of the standard counts. It is believed that gauges having vertically moveable source rods are sensitive to slight changes in radiation source position due to the close proximity of the radiation source 22 to the first radiation detector 16. Due to the relatively long distance or path length between the radiation source 22 and the second radiation detector 18, variability problems are not normally associated with the second radiation detector due to a dampening effect caused by the relatively long distance.

The nuclear gauge 10 of the present invention minimizes the variance in nuclear count rate, and the subsequent variance in measured thin layer density due to this variance, that is attributable to minor source rod positioning changes. Specifically, it is desirable, for a four minute thin layer density measurement, that the first radiation detector 16 count uncertainty due to minor source rod positioning inconsistencies should contribute no more than twenty-five percent of the total observed count uncertainty.

The gauge 10 of the present invention provides a maximum radial movement of less than about 0.003 inch, most preferably less than about 0.002 inch, at any given predetermined source rod 20 position. In other words, the gauge 10 is designed so that the distal end of the source rod 20 containing the radiation source 22 cannot move in a radial or lateral direction more than about 0.003 inch, most preferably less than about 0.002 inch, from the central axis of the vertical cavity 11. Additionally, the gauge 10 of the present invention has a maximum vertical movement of less than about 0.003 inch, and preferably less than about 0.002 inch, at any given source rod position. Thus, for each source rod position, the radiation source position will vary less than about 0.003 inch, preferably less than about 0.002 inch, from the desired radiation source depth.

The gauge handle 28 may be constructed of any suitable material, such as aluminum or stainless steel. Preferably, the gauge handle 28 is constructed of stainless steel. The stainless steel minimizes distortion of the hole into which the source rod 20 is pressed. The machined hole of the gauge handle 28 into which the source rod 20 is pressed is preferably sized as 0.6235±0.0005 inches in diameter to ensure a good fit.

Additionally, to ensure that there is no movement of the source rod 20 within the hole in the gauge handle 28, at least two fasteners 64, such as spring pins, are inserted through the handle 28 and source rod 20 to affix the source rod to the handle. Unlike the use of a single fastener, the use of at least two fasteners does not provide a pivot point about which a source rod 20 may move.

Preferably, the gauge handle 28 has a cavity for the indexer 36 having a diameter of 0.503±0.001 inch. This reduces variance in the source rod position by encouraging stable indexer 36 positioning and movement. The spring rate for the spring 38 that biases the indexer 36 towards the notches 26 of the index rod 24 is at least about twenty pounds per inch, preferably at least about twenty-two pounds per inch. Thus, when the indexer 36 is engaged in a notch 26 of the index rod 24, the force pushing on the indexer is approximately 8.3 lbs.

As shown in FIG. 5, the notches 26 of the index rod 24 comprise a first side surface roughly perpendicular to the axis of the index rod and a bottom surface roughly parallel to the axis of the index rod. Further, the notches 26 include a second side surface having a sloped portion. This notch configuration, in conjunction with the relatively high spring rate of spring 38, allows precise placement of the indexer 36 in the notches 26. If placed adjacent to the sloped portion of a notch 26, the spring-loaded indexer 36 will slide into abutting contact with both the bottom surface of the notch and the first side surface, thereby ensuring consistent indexing of the source rod 20.

Preferably, the trigger 34 has very little clearance in the oblong hole in the handle 28 from which it protrudes. Specifically, the trigger 34 has a diameter of 0.496±0.002 inch and moves laterally within an oblong slot having a width of 0.500±0.002 inch. This result in a clearance range of 0.002 to 0.008 inch. The small resulting clearance of the trigger 34 within the oblong slot prevents rotation of the trigger 34 within the slot that can cause a poor fit of the indexer 36 in the notches 26.

Preferably, there is also very little clearance between the index rod 24 and the hole within the handle 28 through which it passes. The index rod 24 has a diameter of 0.625±0.001 inch and passes through a hole in the handle 28 having a diameter of 0.6270±0.0005 inch, resulting in a diametrical clearance range of only 0.0005 to 0.0035 inch. Note that the nominal diametrical clearance of 0.0020 inch (0.0005±0.0035 divided by 2) is nominally 0.0010 inch radial clearance from true center.

The flat side 42 of the index rod 24 prevents the index rod hole in the handle 28 through which the index rod passes from closely following the index rod. This lack of concentric fit can be a significant source of positioning variability, especially in the backscatter position 32 and standard count position 30. In order to eliminate this source of error, the index rod 24 has a full diameter extending down at least through the position of the backscatter position notch 32. Thus, the full diameter of the index rod 24 extends through the backscatter position and provides a better fit of the index rod to the handle 28. The index rod 24 is shown in greater detail in FIGS. 5A and 5B.

The safe position corresponding to the notch 30 is preferably located at least about 2.20 inches above the outer surface of the base 14 of the gauge housing 12. This places the radiation source 22 in a position that exhibits reduced sensitivity of the standard count to slight radiation source positioning variability in the vertical direction. Specifically, the radiation standard count rate with the radiation source 22 in the safe position changes only about 2.8 counts per mil of radiation source position change in the vertical direction in the gauge 10 of the present invention.

The bearings 44 that guide the source rod 20 through cavity 11 in the gauge housing 12 preferably provide an extremely close fit to the source rod in order to minimize variability in radiation source positioning. Specifically, the outer diameter of bearings 44 is preferably 1.1265+0.0005/−0.000 inch and the bearing inner diameter is preferably 0.6265+0.0005/−0.000 inch. Additionally, the bearing housing diameter is preferably 1.1265±0.0005 inch. The source rod 20 diameter is preferably 0.625±0.001. This results in a nominal bearing clearance of 0.00025 inch and a bearing clearance range of press-fit to 0.001 inch. The nominal source rod 20 clearance is 0.00175 inch and the source rod clearance range is from 0.0005 to 0.0030 inch. Thus, the source rod 20 has a total range of radial movement of no more than about 0.0005 to about 0.0040. Since the desired position of the source rod 20 is on the true centerline of the bearings 44, the movement away from true center is actually the radial clearance, which equals one-half of the diametrical clearance. Thus, the maximum movement away from true center of the source rod 20 is one-half of 0.0040 inch or 0.0020 inch.

As discussed above, the gauge 10 of the present invention preferably includes a safety shield 46. The backscatter position is a position that is particularly sensitive to variations in radiation source positioning. To minimize radial movement of the distal end of the source rod 20, the safety shield 46 preferably includes a bearing 48. The bearing 48 is press-fit into the safety shield 46 and has a through diameter of 0.6265±0.0005 inch. This provides a maximum radial clearance of 0.0015 inch. Thus, there is a maximum of 0.0015 inch radial movement from true centerline by the distal end of the source rod 20 in the backscatter position.

The nuclear gauge 10 advantageously includes a radiation shield assembly that is operatively positioned to move laterally between two positions, a first position blocking a distal end of the vertical cavity 11 of the gauge housing 12 such that radiation is shielded from exiting the cavity and a second position adjacent to the vertical cavity and allowing vertical movement therethrough by the source rod 20. The radiation shield assembly include a sliding block 50 operatively positioned to move laterally between the first position and the second position. The sliding block 50 is shown in greater detail in FIGS. 4A and 4B. As shown, the sliding block 50 preferably includes a chamfer 66 that lessens the effect of radiation source positioning on the count rate measured by the first radiation detector 16 in backscatter mode. A spring 54 engages the sliding block 50 and biases the sliding block into the first position where it blocks the vertical cavity 11 within the gauge housing 12. The spring guide 62 guides one end of the spring 54 while the other end of the spring is engaged with the sliding block 50.

The radiation shield assembly further comprises a fixed block 52. The fixed block 52 is located adjacent to the gauge base 14 and is shown in greater detail in FIGS. 3A and 3B. As shown, the fixed block 52 includes a track 60 which engages the sliding block 50 and guides movement of the sliding block as it moves laterally between the first position to the second position. The fixed block 52 shields the nearest radiation detector 16 from internal gamma rays streaming inside the gauge housing 12 when the source rod 20 is in the backscatter position. The track 60 restricts the side-to-side movement of the sliding block 50 such that the sliding block follows a more stable path between the first position and the second position. Preferably, the sliding block 50 and the fixed block 52 are constructed of lead or tungsten, but other suitable radiation shielding materials may be used.

Referring back to FIG. 2, the gauge 10 preferably comprises a ball plunger 56 engaging the sliding block 50 and operatively positioned to prevent vertical movement of the sliding block as the sliding block moves laterally between the first and second positions. Preferably, the ball plunger 56 is biased towards the sliding block 50 by a spring 58. Since there is a slight gap between the top of the sliding block 50 and the top wall of the cavity creating the housing for the radiation shield assembly, the sliding block has room to move in the vertical direction. The ball plunger 56 prevents the sliding block from rocking upward and downward as it moves between the first and second position, particularly as it retracts when the distal end of the source rod 20 engages the sliding block and forces the sliding block to move into the second position. The ball plunger 56 includes a ball, preferably constructed of steel and having a 3/16" diameter, that provides a point contact on the top surface of the sliding block 50. The spring 58 preferably has a spring rate of at least 50 lbs. per inch such that it pushes the ball plunger 56 downward with a force of about 11 to about 12 lbs. The downward force on the top of the sliding block 50 eliminates any rocking motion and forces the sliding block to move in a horizontal plane.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A nuclear gauge, comprising:
    a gauge housing having a vertical cavity therethrough and a base;
    at least one radiation detector located within said housing and adjacent to said base of said housing;
    a vertically moveable source rod extending into said cavity of said gauge housing;
    a radiation source operatively positioned within a distal end of said source rod;
    means for vertically extending and retracting said source rod to a plurality of predetermined source rod positions so as to change the spatial relationship between said radiation source and said at least one radiation detector; and
    a radiation shield assembly operatively positioned to move laterally between two positions, a first position blocking a distal end of said vertical cavity of said gauge housing such that radiation is shielded from exiting said cavity and a second position adjacent to said vertical cavity and allowing vertical movement therethrough, said radiation shield assembly comprising
        a sliding block operatively positioned to move laterally between said first position and said second position, and
        a fixed block, said fixed block including a track engaging said sliding block and guiding movement of said sliding block.

2. A nuclear gauge according to claim 1, further comprising a ball plunger engaging said sliding block and operatively positioned to prevent vertical movement of said sliding block as said sliding block moves laterally between said first and said second position.

3. A nuclear gauge according to claim 2, further comprising a spring engaging said ball plunger and biasing said ball plunger towards said sliding block.

4. A nuclear gauge according to claim 3, wherein said spring engaging said ball plunger has a spring rate of at least about 50 lbs./inch.

5. A nuclear gauge according to claim 1, wherein both said fixed block and said sliding block are constructed of lead or tungsten.

6. A nuclear gauge according to claim 1, wherein said at least one radiation detector comprises a first radiation detector located at a first position within said housing and adjacent to said base of said housing and a second radiation detector located at a second position within said housing and adjacent to said base of said housing.

7. A nuclear gauge according to claim 1, wherein said means for vertically extending and retracting said source rod comprises an index rod operatively positioned adjacent to said source rod, said index rod including a plurality of notches, each of said notches corresponding to one of said predetermined source rod positions.

8. A nuclear gauge according to claim 7, wherein said means for vertically extending and retracting said source rod further comprises a handle affixed to said source rod, said handle including a cavity therethrough and an indexer, said index rod extending into said cavity of said handle, said indexer operatively positioned for engaging said notches of said index rod in order to temporarily affix said source rod in one of said predetermined positions.

9. A nuclear gauge according to claim 1, wherein said radiation source is a $^{137}$Cs radiation source.

10. A nuclear gauge according to claim 1, wherein said radiation shield assembly further comprises means for biasing said sliding block into said first position.

* * * * *